United States Patent [19]

Shen et al.

[11] 3,956,363

[45] May 11, 1976

[54] SUBSTITUTED INDENYL ACETIC ACIDS

[75] Inventors: Tsung-Ying Shen, Westfield, N.J.;
Richard B. Greenwald, Framingham, Mass.; Howard Jones, Holmdel, N.J.; Bruce O. Linn, Somerville, N.J.; Bruce E. Witzel, Westfield, N.J.

[73] Assignee: Merck & Co., Inc., Rahway, N.J.

[22] Filed: Aug. 23, 1974

[21] Appl. No.: 499,870

Related U.S. Application Data

[60] Continuation of Ser. No. 478,548, June 11, 1974, Pat. No. 3,888,902, which is a continuation of Ser. No. 301,914, Oct. 30, 1972, abandoned, which is a division of Ser. No. 187,197, Oct. 6, 1971, Pat. No. 3,725,548, which is a division of Ser. No. 33,981, May 1, 1970, Pat. No. 3,654,349, which is a continuation-in-part of Ser. No. 848,736, Aug., 1969, abandoned.

[52] U.S. Cl. .................. 260/479 R; 260/470; 260/501.1; 260/501.11; 260/501.16; 260/501.21; 260/515 A; 260/515 M; 260/518 A; 260/519; 260/476 R

[51] Int. Cl.$^2$ ............................................. C07C 63/50
[58] Field of Search ........ 260/479 R, 518 R, 518 A, 260/519, 470, 476

[56] References Cited

UNITED STATES PATENTS 3,312,730   4/1967   Winter et al. ...................... 260/473

Primary Examiner—James A. Patten
Attorney, Agent, or Firm—Mario A. Monaco; Harry E. Westlake, Jr.

[57] ABSTRACT

New substituted indenyl acetic acids and nontoxic pharmaceutically acceptable amides, esters and salts derived therefrom. The substituted indenyl acetic acids disclosed herein have anit-inflammatory, antipyretic and analgesic activity.

5 Claims, No Drawings

SUBSTITUTED INDENYL ACETIC ACIDS

CROSS REFERENCE TO RELATED APPLICATIONS

This application is a continuation of U.S. Ser. No. 478,548 filed June 11, 1974, now U.S. Pat. NO. 3,888,902, which is a continuation of U.S. Ser. No. 301,914 filed Oct. 30, 1972, now abandoned, which is a division of co-pending U.S. Ser. No. 187,197 filed Oct. 6, 1971, which issued to U.S. Pat. No. 3,725,548 on Apr. 3, 1973 which, in turn, is a division of co-pending U.S. Ser. No. 33,891 filed May 1, 1970, which issued to U.S. Pat. No. 3,654,349 on Apr. 4, 1972 which, in turn, is a continuation-in-part of U.S. Ser. No. 848,736 filed Aug. 8, 1969, now abandoned.

BACKGROUND OF THE INVENTION

The development of anit-inflammatory compounds in the past two decades has seen the growth of a great many new drugs. Most of these have been steroids of the 11-oxygenated pregnane series. These, while highly effective as anti-inflammatory agents, have many side effects. More recently, nonsteroidal anti-inflammatory compounds, such as the indenyl, indolyl and salicylic acids, of much simpler structure than the steroidal anti-inflammatory compounds have been developed.

An object of this invention is the development of new potent anti-inflammatory and analgesic compounds.

SUMMARY OF THE INVENTION

Generally, this invention relates to new substituted indenyl acetic acid compounds having an acyloxy, acylamino and/or a cyano group on the phenyl group of the indenyl moiety.

DESCRIPTION AND PREFERRED EMBODIMENTS

This invention relates to new substituted indenyl acetic acids, and more specifically, to substituted indenyl acetic acids, amides, esters and non-toxic pharmaceutically acceptable salts thereof. Still more specifically, this invention relates to the compounds having the following general formula:

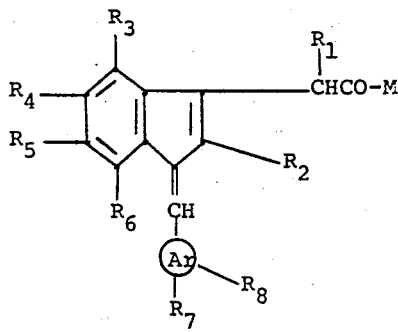

I wherein
Ar may be aryl or heteroaryl;
$R_1$ may be hydrogen, $C_{1-5}$ loweralkyl or halogenated $C_{1-5}$ loweralkyl;
$R_2$ may be hydrogen or $C_{1-5}$ loweralkyl;
$R_3$, $R_4$, $R_5$ and $R_6$ each may be hydrogen, $C_{1-5}$ loweralkyl, acyloxy, $C_{1-5}$ loweralkoxy, nitro, amino, acylamino, $C_{1-5}$ loweralkylamino, di-$C_{1-5}$ loweralkylamino, di-$C_{1-5}$ loweralkylamino $C_{1-5}$loweralkyl, sulfamyl, $C_{1-5}$loweralkylthio, mercapto, hydroxy, hydroxy $C_{1-5}$ alkoxy, $C_{1-5}$loweralkylsulfinyl, $C_{1-5}$ loweralkylsulfonyl, halogen, cyano, carboxyl, carb $C_{1-5}$loweralkoxy, carbamido, halogeno-$C_{1-5}$ loweralkyl, cycloalkyl or cycloalkoxy, alkynyl, alkenyl, aroyl, at least on of $R_3$, $R_4$, $R_5$ and $R_6$ being acyloxy, acylamino or cyano;
$R_7$ may be $C_{1-5}$ alkylsulfinyl or $C_{1-5}$ alkylsulfonyl;
$R_8$ may be hydrogen, halogen, hydroxy, $C_{1-5}$ loweralkoxy, or halo-$C_{1-5}$ loweralkyl; and
M may be hydroxy, $C_{1-5}$ loweralkoxy, substituted $C_{1-5}$ loweralkoxy, amino, $C_{1-5}$ alkylamino, $C_{1-5}$ diloweralkylamino, N-morpholino, hydroxy $C_{1-5}$ loweralkylamino, polyhydroxy $C_{2-6}$ loweralkylamino, di $C_{1-5}$ loweralkylamino $C_{1-5}$ alkylamino, amino $C_{1-5}$ loweralkylamino, and the group OMe, in which Me is a cation.

The indene nucleus may be substituted in the 1-position by an aryl ring system such as benzene, naphthalene or biphenyl or a heteroaryl ring system such as a pyrrole, furan, thiophene, pyridine, imidazole, pyrazine, thiazole, etc. which contains an alkylsulfinyl or alkylsulfonyl substituent and may be further substituted with a halogen (chloro, fluoro or bromo), hydroxy, alkoxy (methoxy, ethoxy, propoxy, etc.) or haloalkyl (fluoromethyl, chloromethyl, trifluoromethyl, etc.) group.

More specifically $R_3$, $R_4$, $R_5$ and $R_6$ and M of formula I are as follows:

$R_3$, $R_4$, $R_5$ and $R_6$ are each hydrogen, $C_{1-5}$ loweralkyl, $C_{1-5}$ loweralkanoyloxy, benzyloxy, $C_{1-5}$ loweralkoxy, nitro, amino, $C_{1-5}$ loweralkanoylamino, benzoylamino, $C_{1-5}$ loweralkylamino, di-$C_{1-5}$ loweralkylamino, di-$C_{1-5}$ loweralkylaminoalkyl, sulfamyl, $C_{1-5}$ loweralkylthio, mercapto, halogen, hydroxy, hydroxy $C_{1-5}$ loweralkyl, $C_{1-5}$ loweralkylsulfonyl, carboxyl, carb $C_{1-5}$ loweralkoxy, carbamido, halogeno or $C_{1-5}$ loweralkyl, at least one of $R_3$-$R_6$ being $C_{1-5}$ loweralkanoyloxy, benzyloxy, $C_{1-5}$ loweralkanoylamino or benzoylamino; and M may be hydroxy, $C_{1-5}$ loweralkoxy, amino, $C_{1-5}$ loweralkylamino, di-$C_{1-5}$ loweralkylamino, N-morpholino, hydroxy $C_{1-5}$ loweralkymamino, polyhydroxy $C_{2-5}$ loweralkylamino and the pharmaceutically acceptable acid salts.

In the most preferred compounds of this invention $R_1$ is hydrogen or $C_{1-5}$ loweralkyl, and especially hydrogen; $R_2$ is $C_{1-5}$ loweralkyl and especially methyl; $R_3$, $R_4$, $R_5$ and $R_6$ are each hydrogen, $C_{1-5}$ loweralkanoyloxy, benzoyloxy, $C_{1-5}$ loweralkanoylamino, benzoylamino, cyano, fluoro, $C_{1-5}$ loweralkoxy or di-$C_{1-5}$ loweralkylamino, no more than two of $R_3$, $R_4$, $R_5$ and $R_6$ being other than hydrogen; and especially acetyloxy, acetylamino or cyano; Ar is phenyl; $R_7$ is methylsulfinyl or methylsulfonyl and especially methylsulfinyl; $R_8$ is hydrogen; and M is hydroxy or $C_{1-5}$ loweralkoxy, and especially hydroxy.

Representative compounds of this invention are as follows:
5-Cyano-2-methyl-1-p-methylsulfinylbenzylidene-3-indene acetic acid;
6-Cyano-2-methyl-1-p-methylsulfinylbenzylidene-3-indene acetic acid;
7-Cyano-2-methyl-1-p-methylsulfinylbenzylidene-3-indene acetic acid;
α-(5-Cyano-2-methyl-1-p-methylsulfinylbenzylidene-3-indene)propionic acid;

5,6-diCyano-2-methyl-1-p-methylsulfinylbenzylidene-3-indene acetic acid;
5-Acetyloxy-2-methyl-1-p-methylsulfinylbenzylidene-3-idene acetic acid;
5-Acetylamino-2-methyl-1-p-methylsulfinylbenzylidene-3-indene acetic acid;
5,6-diCyano-2-methyl-1-p-methylsulfonylbenzylidene-3-indene acetic acid;
5,7-Dicyano-2-methyl-1-p-methylsulfinylbenzylidene-3-indene acetic acid;
α-(5,7-Dicyano-2-methyl-1-p-methylsulfinylbenzylidene-3-indene)propionic acid;
5-Fluoro-6-cyano-2-methyl-1-p-methylsulfinylbenzylidene-3-indene acetic acid;
5-Fluoro-6-acetyloxy-2-methyl-1-p-methylsuflinylbenzylidene-3-indene acetic acid;
α-(5-Fluoro-6-acetyloxy-2-methyl-1-p-methylsulfinylbenzylidene-3-indene)propionic acid;
α-(5,6-Dicyano-2-methyl-1-p-methylsulfinylbenzylidene-3-indene)propionic acid;
5-Cyano-2-methyl-1-p-methylsulfonylbenzylidene-3-indene acetic acid;
5-Acetyloxy-2-methyl-1-p-methylsulfonylbenzylidene-3-indene acetic acid;
5-Acetylamino-2-methyl-1-p-methylsulfonylbenzylidene-3-indene acetic acid;
and the corresponding amides, esters and salts.

It should be noted that the compounds of this invention may be isomerized into their cis and trans isomers by procedures well known in the art. Accordingly, it is to be understood that reference throughout the specification anad appended claims to the compounds of this invention is intended to encompass not merely the compounds per se but includes their geometric isomers (cis, trans).

It should be further noted by one skilled in the art that the alkylsulfinyl derivatives of this invention are racemic mixtures of optically active enantiomorphs which may be resolved into their (+) and (−) forms by techniques well known in the art. Furthermore, when $R_1$ is loweralkyl an additional asymmetric atom results which gives rise to two additional enantiomorphs, which are also considered to be within the scope of the invention.

One skilled in the art should further note that some of the compounds of this invention are polymorphic and have different crystalline structures, melting points and solubility characteristics.

The compounds of the instant invention can be used to treat inflammation by reducing inflammation and relieving pain in such diseases as rheumatoid arthritis, osteoarthritis, gout, infectious arthritis and rheumatic fever. The compounds of the instant invention are substantially more water-soluble than similar prior art compounds.

The compounds of Formula I also have anti-pyretic and analgesic activity and would be administered and used in the same manner and in the same dosage ranges as if they were being used to treat inflammation as discussed further on.

The treatment of inflammation employing the compounds of the present invention is accomplished by topically, orally, rectally or parenterally administering to patients a composition of a compound of FOrmula I, particularly the especially preferred compounds in a non-toxic pharmaceutically acceptable carrier.

The non-toxic pharmaceutical carrier may be, for example, either a solid or a liquid. Exemplary of solid carriers are lactose, corn starch, gelatin, talc, sterotix, stearic acid, magnesium stearate, terra albal, sucrose, agar, pectin, cab-o-sil, and acacia. Exemplary of liquid carriers are peanut oil, olive oil, sesame oil and water. Similarly, the carrier or diluent may include a time delay material such as glyceryl monostearate or glyceryl distearate alone or with a wax.

Several pharmaceutical forms of the therapeutically useful compositions can be used. For example if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, an aqueous solution or a liquid suspension. Suppositories may be prepared in a conventional manner by mixing the compounds of this invention with a suitable non-irritating excipient which is solid at room temperature, but liquid at the rectal temperature. Such materials are cocoa butter and polyethylene glycol. Gels and lotions for topical application may be prepared in conventional manners.

The active compounds of Formula I and of the compositions of this invention are administered in an amount sufficient to treat inflammation, that is to reduce inflammation. Advantageously, the compositions will contain the active ingredient, namely, the compounds of Formula I in an amount of from about 0.1 mg. to 50 mg. per kg. body weight per day (5. mg. to 3.5 g. per patient per day), preferably from about 1 mg. to 15 mg./kg. body weight per day (50 mg. to 1 g. per patient per day).

The compounds of Formual I and particularly the especially preferred compounds will be administered in an amount of from 0.1 mg. to 50 mg./kg. body weight per day preferably from about 1 mg. to about 15 mg. per kilogram body weight per day. The most rapid and effective antiinflammatory effect is obtained from oral administration of a daily dosage of from about 1 to 15 mg./kg./day. It should be understood, however, that although preferred dosage ranges are given, the dose level for any particular patient depends upon the activity of the specific compound employed. Also many that factors hat modify the actions of drugs will be taken into account by those skilled in the art in the therapeutic use of medicinal agents, particularly those of Formula I, for example, age, body weight, sex, diet, time of administration, route of administraton, rate of excretion, drug combination, reaction sensitivities and severity of the particular disease.

In the preparation of the compounds of this invention the starting material is a β-aryl propionic acid. Thus, a substituted benzyladehyde may be condensed with a substituted acetic ester in a Claisen Reaction or with an α-halogenated propionic ester in a Reformatsky Reaction. The resulting unsaturated ester is reduced and hydrolyzed to give the benzyl propionic acid starting material. Alternatively, a substituted malonic ester in a typical malonic ester synthesis and acid hydrolysis of the resulting substituted ester yields the benzyl propionic acid directly or the benzaldehyde maybe reacted with propionic anhydride in a reducing medium to form the benzyl propionic acid.

In the preparation of the compounds of the instant invention, again a number of routes are possible. The first step is ring closure of the β-aryl propionic acid to form an indanone which may be carried out by a Friedel-Crafts Reaction using a Lewis acid catalyst or by heating with polyphosphoric acid. The indanone may be condensed with an α-halo ester in the Reformatsky Reaction to introduce the aliphatic acid side chain by replacing the carbonyl group. Alternatively, this introduction can be carried out by the use of a Wittig Reaction in which the reagent is an α-triphenylphosphinyl ester, a reagent which replaces the carbonyl with a double bond to a carbon. This is immediately rearranged into the indene. If the Reformatsky Reaction route is used, the intermediate 3-hydroxy-3-aliphatic acid derivatives must be dehydrated to the indene. The introduction of the 1-substituent is carried out in one of two ways. The first is the direct reaction of the indene with the aldehyde of the structural characteristics defined, using a strong base as a catalyst and warming, if necessary, to form the carbanion. The reaction can be carried out in a number of solvents such as polar solvents like dimethoxyethane, aqueous methanol, puridine, liquid ammonia, dimethylformamide and the like or even in non-polar solvents such as benzene, etc. Alternatively, an indanone can be brominated and then dehydrogenbrominated to an indenone and the indenone carbonyl replaced by the substituent using the α-triphenyl-phosphinyl compounds of the desired structure. In this manner, the loweralkyl ester of the desired compound is obtained. This ester can then be hydrolyzed to give the free acids and oxidized to give the sulfoxides and sulfones from which the salts, other esters and the amides may be formed. Alternatively, the 1-unsubstituted 3-indenyl ester may be hydrolyzed to the free acid followed by the condensation reaction to lead to the free acid compounds of this invention.

ALthough in one synthesis described above the esters of the acids are produced, some desired esters are more easily obtained by forming a simple ester of the final acid, hydrolyzing to the free acid and re-esterifying. The simple loweralkyl or benzyl esters are usually the ones used in the synthesis of the compounds. Other esters are more desirable from the standpoint of therapeutic utility of the compounds, such as the methoxymethyl, diethylaminoethyl, dimethylaminoethyl, dimethylaminopropyl, diethylaminopropyl, N-pyrollidinylethyl, N-piperidinylethyl, N-morpholinylethyl, N-ethyl-2-piperidinylethyl, N-pyrollidinylmethyl, N-methyl-2-pyrrolidinylmethyl, 4-methyl-1-piperazinylethyl, methoxyethyl, ethoxyethyl, and the like. These are mostly prepared from the corresponding alcohol and the indenyl acid.

The amides, both the simple amide and the substituted amides, are similarly prepared from the indenyl acids and the corresponding amines. Especially useful therapeutically are the morpholide, the bis(hydroxyethyl)amide and the like.

Similarly, salts are obtained by neutralizing the indenyl acids with bases or by methathesis of other salts. Especially useful are the metallic salts such as the alkali metal or alkaline earth salts and the amine and quaternary ammonium salts, which are water soluble, but the heavy metal salts such as iron, alumminum, etc. are also useful for some purposes.

The following examples are presented to further illustrate the invention:

EXAMPLE 1

A. α-Methyl-β-(p-cyanophenyl)propionic acid

To a solution of 2.3 g. (0.1 mole) of sodium in 100 ml. of absolute alcohol is added 17.4 g. (0.1 mole) of diethyl methylmalonate and (0.1 mole) of p-cyanobenzylchloride. The mixture is heated under a reflux in a water bath for 3 hours. The reaction mixture is poured into water and the aqueous solution is extracted 6 times with ether and dried. It is then evaporated to yield diethyl methyl-p-cyanobenzyl malonate. The crude product is then saponified by heating with excess 4% sodium hydroxide in aqueous ethanolic solution. The solution thus formed is concentrated, extracted with ether to remove any neutral material, and acidified with dilute sulfuric acid. The acidic mixture is heated on a steam bath for 1 hour, cooled and then extracted with ether. Evaporation of the ether solution gives α-methyl-β-(p-cyanophenyl)propionic acid.

In a similar manner, using other substituted malonic esters in place of diethyl methylmalonate and other substituted benzyl halides in place of p-cyanobenzyl chloride, the corresponding substituted propionic acids are obtained, for example:

α-methyl-β-(p-acetylaminophenyl)propionic acid,
α-allyl-β-(p-cyanophenyl)propionic acid,
α-methyl-β-(p-acetyloxyphenyl)propionic acid.

Similarly, when p-cyano-m-fluorobenzylchloride, p-acetyloxy-m-fluorobenzylchloride, p-acetylamino-m-fluorobenzylchloride, p-cyano-m-methoxybenzylchloride, m-cyano-p-dimethylaminobenzylchloride, p-cyano-O-fluorobenzylchloride, p-acetylamino-m-methoxybenzylchloride, p-benzoyloxybenzylchloride, p-benzoylaminobenzylchloride, m,p-dicyanobenzylchloride, m,p-diacetylaminobenzylchloride, or m,p-diacetyloxybenzylchloride is used in place of p-cyanobenzylchloride, there is obtained α-methyl-β-(p-cyano-m-fluorophenyl)-propionic acid
α-methyl-β-(p-acetyloxy-m-fluorophenyl)-propionic acid
α-methyl-β-(p-acetylamino-m-fluorophenyl)-propionic acid
α-methyl-β-(p-cyano-m-methoxyphenyl)-propionic acid
α-methyl-β-(m-cyano-p-dimethylaminophenyl)-propionic acid
α-methyl-β-(p-cyano-O-fluorophenyl)-propionic acid
α-methyl-β-(p-acetylamino-m-methoxyphenyl)-propionic acid
α-methyl-β-(p-benzoyloxyphenyl)-propionic acid
α-methyl-β-(p-benzoylaminophenyl)-propionic acid
α-methyl-β-(m,p-dicyanophenyl)-propionic acid
α-methyl-β-(m,p-diacetylaminophenyl)-propionic acid or
α-methyl-β-(m,p-diacetyloxyphenyl)-propionic acid.

B. 6-Cyano-2-methylindanone

α-Methyl-β-(p-cyanophenyl)propionic acid (14.5 g.) is added to 170 g. of polyphosphoric acid at 50° and the mixture is heated at 83°–90° for two hours. The syrup is poured into iced water, stirred for one-half hour and then extracted with ether three times. The ether solution is washed with water twice and 5% NaHCO₃ five times until all the acidic material has been removed. The remaining neutral solution is washed with water and dried over sodium sulfate. Evaporation of the solution gives the indanone, m.p. 95°–95°.

In a similar manner, the other β-aryl propionic acid compounds are converted to the corresponding indanone by the procedure of this example.

C. Methyl-5-cyano-2-methyl-3-indenylacetate

A solution of 13.0 g. of 6-cyano-2-methylindanone and 19.3 g. of methyl bromoacetate in 45 ml. benzene is added over a period of 5 minutes to 21 g. of zinc amalgam (prepared according to *Org. Syn. Coll.*, Vol. 3) in 110 ml. benzene and 40 ml. dry ether. A few crystals of iodine are added to start the reaction, and the reaction mixture is maintained at reflux temperature (ca. 65°) with external heating. At 3 hour intervals two batches of 10 g. zinc amalgam and 10 g. bromoester are added and the mixture is then refluxed for 8 hours. After addition of 30 ml. of ethanol and 150 ml. of acetic acid, the mixture is poured into 700 ml. of 1:1 aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temp.) (1-2 mm.) gives crude methyl (1-hydroxy-2-methyl-5-cyano-indenyl)acetate.

A mixture of the above crude hydroxyester, 20 g. of p-toluenesulfonic acid monohydrate and 20 g. of anhydrous calcium chloride in 250 ml. of toluene is refluxed overnight. The solution is filtered and the solid residue is washed with benzene. The combined benzene solution is washed with water, sodium bicarbonate, water and then dried over sodium sulfate. After evaporation the crude methyl-5-cyano-2-methyl-3-indenylacetate is chromatographed on acid-washed alumina, and the product is eluted with petroleum ether-ether (v/v 50-100%), m.p. 70°-75° from ether-hexane.

Methyl 6-cyano-2-methyl-3-indenylacetate

The above reactions of Example 1C are repeated except that the starting materials are 2-methyl-5-cyanoindanone and methylbromoacetate. Using the same reaction conditions and techniques there is obtained methyl 2-methyl-6-cyano-3-indenylacetate.

When any of the other indanones described above are used in the above procedure in place of 6-cyano-2-methylindanone the corresponding methyl ester is obtained.

D. 5-Cyano-2-methyl-1-(p-methylthiobenzylidene)-3-indenyl acetic acid

To a solution of methyl 5-cyano-2-methyl-3-indenylacetate (0.037 mole) and p-methylthiobenzaldehyde, 6.3 g. (1.1 equivalent) is added 16$^+$ ml. (2.0$^+$ equivalents) of 25% methanolic sodium methoxide. The mixture is stirred at reflux under nitrogen for 2 hours. An equal volume of water is added dropwise and refluxing continues for 30 minutes. The solution is cooled, diluted with water and extracted with ether (3X). Residual ether is blown off with nitrogen and then the aqueous solution is acidified with 50 glacial acetic acid. The precipitated product is collected and washed thoroughly with water. The crude product is crystallized from methanol to give pure 5-cyano-2-methyl-1-(p-methylthiobenzylidene)-3-indenyl-acetic acid.

The other methyl esters of Example 1C are reacted with p-methylthiobenzaldehyde according to the above procedure to produce the ocrresponding indenyl acetic acid.

E. 5-Cyano-2-methyl-1-(p-methylsulfinylbenzylidene)-3-indenylacetic acid

A solution of sodium periodate (0.214 g.) (0.001 mole) in 3 ml. of water is added dropwise to 5-cyano-2-methyl-1-(p-methylthiobenzylidene)-3-indenylacetic acid (0.001 mole) in 25 ml. methanol and enough acetone to cause solution. This solution is stirred overnight at room temperature and filtered. The filtrate is evaporated at 30° to a small volume which causes the product to precipitate. The suspension is diluted with several volumes of water, cooled and collected. The product is dried in vacuo over potassium hydroxide pellets and then in a vacuum oven at 70° to give 5-cyano-2-methyl-1-(p-methylsulfinylbenzylidene)-3-indenylacetic acid, m.p. 160°-155° in from ethyl acetate.

5-Cyano-2-methyl-1-(p-methylsulfonylbenzylidene)-3-indenylacetic acid is prepared by the addition of 1.0 mole of m-chloroperbenzoic acid per mole of 5-cyano-2-methyl-1-(p-methylsulfinylbenzylidene)-3-indenylacetic acid in an acetone solution.

EXAMPLE 2

A. 6-Cyano-2-methylindanone

In a 500 ml. 3-necked flask is placed 36.2 g. (0.55 mole) of zinc dust and in a 250 ml. addition funnel is charged a solution of 80 ml. anhydrous benzene, 20 ml. of anhydrous ether, (0.58 mole) of p-cyanobenzaldehyde and 98 g. (0.55 mole) of ethyl-2-bromopropionate. About 10 ml. of the solution is added to the zinc dust with vigorous stirring and the mixture is warmed gently until an exothermic reaction commences. The remaining reactants are added dropwise at such a rate that the reaction mixture is refluxing smoothly on its own accord (ca. 30–35 min.). After addition is completed the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid and washed twice with 50 ml. portions of water. The aqueous acidic layers are combined and extracted with 2 × 50 ml. ether. The combined etheral and benzene extracts are dried over sodium sulfate. Evaporation of solvent and fractionation of the residue through a 6 inch Vigreux column affords the product, ethyl 2-hydroxy-(p-cyanophenyl)-1-methylpropionate.

By the method described in Vander Zanden, *Rec. trav. chim.*, 68, 413 (1949), the above compound is converted to 6-cyano-2-methylindanone, m.p. 94°-95° from ether hexane.

B. 5-Cyano-2-methyl-1-(p-methylsulfinylbenzylidene)-3-indenylacetic acid

The reactions of Example 1C, 1D and 1E are repeated and 5-cyano-2-methyl-1-(p-methylsulfinylbenzylidene)-3-indenylacetic acid is obtained, m.p. 160°-165° from ethyl acetate.

EXAMPLE 3

A. Methyl α-(5-cyano-2-methyl-3-indenyl)propionate

The procedure of Example 1C is followed using methyl α-bromopropionate in equivalent quantities in place of methyl bromoacetate used therein. There is obtained methyl α-(1-hydroxy-6-cyano-2-methyl-1-indenyl)propionate and it is then dehydrated to methyl α-(5-cyano-2-methyl-3-indenyl)propionate in the same manner.

B.

α-[1-(p-Methylthiobenzylidene)-2-methyl-5-cyano-3-indenyl]propionic acid

To a solution of (0.00192 mole) of methyl α-(5-cyano-2-methyl-3-indenyl)propionate and 0.595 g. (0.0039 mole) of p-methylthiobenzaldehyde in 3 ml. of anhydrous pyridine is added 1.63 g. of 40% solution of benzyltrimethylammonium hydroxide (Triton-B) in methanol. The resulting red-purple solution is allowed to stir at room temperature overnight.

The reaction mixture is poured into a mixture of ice and water, acidified with 2.5N HCl, and extracted with ether. The ether solution is then washed with 2.5 N HCl until the washing acidifies (once), then with water until neutral. The ether layer is then extracted with 5% $Na_2CO_3$ solution. The $Na_2SO_3$ solution is washed with ether, acidified and extracted with ether. The ether solution is washed with water, dried over $Na_2So_4$, and concentrated in vacuo to yield the product.

C.

α-[1-(p-Methylsulfinylbenzylidene)-2-methyl-5-cyano-3-indenyl]-propionic acid

The procedure of Example 1E is followed using α-[1-(p-methylthiobenzylidene-2-methyl-5-cyano-3-indenyl]-propionic acid in place of 5-cyano-2-methyl-1-(p-methylthiobenzylidene)-3-indenylacetic acid thereby producing α-[1-(p-methylsulfinylbenzylidene)-2-methyl-5-cyano-3-indenyl]-propionic acid.

α-[1-(p-Methylsulfonylbenzylidene)-2-methyl-5-cyano-3-indenyl]-propionic acid is produced by the addition of 1.0 mole of m-chloroperbenzoic acid per mole of α-[1-(p-methylsulfinylbenzylidene)-2-methyl-5-cyano-3-indenyl]-propionic acid as described in Example 1E.

EXAMPLE 4

A.

Cis-methyl-5-cyano-2-methyl-1-(p-methylthiobenzylidene)-3-indenylacetate isolation by column chromatography Four drops of concentrated sulfuric acid is added to a solution of 5-cyano-2-methyl-1-(p-methylthiobenzylidene)-3-idenylacetic acid, (2.8 mmole) in 60 ml. of dry methanol and the solution stirred at reflux overnight. The solution is cooled and crystals separated which are collected rinsed with cold methanol-water (1:1) and dried over potassium hydroxide pellets. These crystals are found to be ca. 95% of the trans-isomer and could be further purified by recrystallizing from methanol giving the trans-isomer. Powdered potassium bicarbonate is added to the filtrate from the first crop of crystals, followed by water. A second crop of mixed ester is obtained in this way which is cis-enriched and used for chromatography.

1.7 G. or cis and trans-mixed esters are chromatographed on a column (3.0 × 90 cm.) of silica-gel, 250 g. of J. T. Baker 3405, packed in methylene chloride-petroleum ether (1:9). The column is developed and eluted with a 1:4 ratio of the same solvents, to yield cuts of the cis and trans-isomer.

B.

Cis-5-cyano-2-methyl-1-(p-methylthiobenzylidene)-3-indenylacetic acid 1.0 N aqueous sodium hydroxide 3.0 ml. (3.0 mmole) is added to cis -methyl 5-cyano-2-methyl-1-(p-methylthiobenzylidene)-3-indenylacetate, (0.64 mmole) in 20 ml. methanol under nitrogen. The mixture is refluxed for 1 hour, cooled, diluted with water and acidified with several ml. of 50% acetic acid. Crystals form and after further chilling in ice bath they are collected, worked thoroughly with water and sucked nearly dry. The product is recrystallized from methanol-water, dried over potassium hydroxide pellets in vacuum dessicator and finally in a vacuum oven at 100°. In this way cis-5-cyano-2-methyl-1-(p-methylthiobenzylidene)-3-indenylacetic acid is obtained.

C.

Cis-5-cyano-2-methyl-1-(p-methylsulfinylbenzylidene)-3-indenylacetic acid

Sodium periodate 214 mg. (1.0 mmole) in 2 ml. water is added to cis-5-cyano-2-methyl-1-(p-methylthiobenzylidene)-3-indenylacetic acid, (0.475 mmole) in 12 ml. of methanol and ca. 0.5 ml. acetone at room temperature. The mixture is stirred overnight, then filtered and concentrated to a small volume without heating and diluted with water. The product is collected, rinsed with water and dried over potassium hydroxide pellets in a vacuum dessicator and finally in the oven dessicator at 80°. The product is recrystallized from ethyl acetate-petroleum ether and gives pure cis-5-cyano-2-methyl-1-(p-methylsulfinylbenzylidene-3-indenyl-acetic acid.

EXAMPLE 5

5-Cyano-2-methyl-1-(p-methylsulfinylbenzylidene)-3-indenylacetmorpholide

A mixture of 5-cyano-2-methyl-1-(p-methylsulfinyl-benzylidene)-3-indenylacetic acid (0.01 mole) and thionyl chloride (0.03 mole) in a dried flask, condenser and drying tube set-up is heated on the steam bath until evolution of gas ceases. Excess thionyl chloride is then removed in vacuo, the residue taken up in a slight excess of anhydrous ether and added slowly to a vigorously stirred, ice-cooled solution of dry morpholine (0.035 mole) in 100 ml. of ether. The mixture is stirred overnight at room temperature, filtered, the morpholine hydrochloride washed with excess ether, and the combined ether filtrates washed with 2 × 100 ml. water, dried over anhydrous sodium sulfate, filtered and the ether removed in vacuo. Chromatography of the crude product on a silica-gel column, using v./v. 50–100% ether in petroleum ether as eluent gives the desired morpholide.

Similarly, when morpholine is replaced by an equivalent amount of the following amines, the corresponding amides are obtained.
Dimethylamine
Ethanolamine
Benzylamine
N,N-diethylethylenediamine
Benzylglycinate
Piperidine
Pyrrolidine
N-methylpiperazine
N-phenylpiperazine N-hydroxyethylpiperazine
Piperazine
Diethylamine
Diethanolamine
Aniline
p-Ethoxyaniline
p-Chloroaniline
p-Fluoroaniline
p-Trifluoromethylaniline
Butylamine
Cyclohexylamine
Methylamine
D-glucosamine
Tetra-o-acetyl-d-glucosamine
D-galactosylamine
D-mannosylamine
N,N-dimethyl-glycine amide
N,N-dibutylglycine aminde
N-methyl-2-aminomethylpiperidine
N-methyl-2-aminomethylpyrrolidine
β-Ethoxyethylamine
Di(β-ethoxyethyl)amine
β-Phenethylamine
α-Phenethylamine
Dibenzylamine
D-mannosamine

EXAMPLE 6

Esters of 5-cyano-2-methyl-1-(p-methylsulfinylbenzylidene)-3-indenylacetic acid

A. Simple Esters - A mixture of .1 mole of 5-cyano-2-methyl-1-(p-methylsulfinylbenzylidene)-3-indenylacetic acid, .2 g. of p-toluene sulfonic acid, 100 ml. of absolute ethanol and 75 ml. of dry benzene is refluxed on a steam bath while slowly distilling the solvent. After 17 hours the residual solvent is removed under reduced pressure. The residue is slurried in aqueous sodium bicarbonate and then with water until neutral. The resulting ethyl ester may be recrystallized from organic solvents such as ethyl acetate, benzene and the like. When methanol, propanol, t-butanol and benzyl alcohol are used instead of the ethanol in the above procedure, there is obtained the corresponding methyl, propyl, t-butyl and benzyl esters.

B. Alkoxyalkyl Esters - Chloromethyl methyl ether (0.055 mole) is added to a suspension of 5-cyano-2-methyl-1-(p-methylsulfinylbenzylidene)-3-indenylacetic acid (0.05 mole) and anhydrous potassium carbonate (0.15 mole) in 250 ml. of anhydrous acetone. The mixture is allowed to stir overnight at room temperature. Diethyl ether is added (about 200 ml.) and the mixture is filtered. The filtrate is washed once with 100 ml. of water and dried over anhydrous sodium sulfate. It is then filtered and the solvent is removed in vacuo. The residue is chromatographed on 200 g. of acid-washed alumina, using ether-petroleum ether (varying from 10–60% ether by volume) as the eluent, to give methoxymethyl 5-cyano-2-methyl-1-(p-methylsulfinylbenzylidene)-3-indenylacetate.

C. Dialkylaminoalkly Esters - A solution of 0.054 mole of N,N'-dicyclohexylcarbodiimide in 6 ml. of anhydrous tetrahydrofuran in added to a solution of 5-cyano-2-methyl-1-(p-methylsulfinylbenzylidene)-3-indenylacetic acid (0.005 mole) and 2-diethylaminoethanol (0.0054 mole) in 17 ml. of anhydrous tetrahydrofuran. The mixture is stirred at ambient temperature overnight. The dicyclohyxylurea is removed by filtration and 2 ml. of glacial acetic acid is added to the filtrate. After the mixture has stood for 1 hour, it is filtered and 200 ml. of ether is added to the filtrate. The solution is then extracted three times with 100 ml. of 2.5 n HCl and the extracts are combined, washed twice with 100 ml. of ether, ice-cooled, made slightly alkaline with concentrated NH₄OH and extracted 3 times with 100 ml. of ether. The ether extracts are combined, washed 10 times with 100 ml. of water to remove traces of starting amine, dried over anhydrous potassium csrbonate, filtered and evaporated in vacuo. The oily residue is β-diethylaminoethyl 5-cyano-2-methyl-1-(p-methylsulfinylbenzylidene)-3-indenylacetate.

When 2-dimethylaminoethanol, 3-dimethylamino-1-propanol, 3-diethylamino-1-propanol, N-β-hydroxyethylpiperidine, N-β-hydroxyethylpyrrolidine, N-hydroxymethylpyrrolidine, N-methyl-2-hydroxymethyloyrrolidine, N-ethyl-2-hydroxymethylpiperidine, 1-β-hydroxyethyl-4'-methylpiperazine or N-β-hydroxyethyl morpholine is used in the above procedure in place of 2-diethylaminoethanol, the corresponding β-dimethylaminoethyl, γ-dimethylaminopropyl, γ-diethylaminopropyl, β-N-piperidinylethyl, β-N-pyrrolidinylethyl, N-pyrrolidinylmethyl, 2'-(1'-methylpyrrolidinylmethyl), 4-methyl-1-piperazinylethyl, N-ethyl-2-piperidinylethyl and N-morpholinylethyl esters are obtained.

D. Phenyl 5-cyano-2-methyl-1-(p-methylsulfinylbenzylidenyl)-3-indenylacetate - A solution of 0.0054 mole of N,N'-dicyclohexylcarbodiimide in 6 ml. of anhydrous tetrahydrofuran is added to a solution of 5-cyano-2-methyl-1-(p-methylsulfinylbenzylidenyl)-3-indenylacetic acid (0.005 mole) and phenol (0.054 mole) in 17 ml. of anhydrous tetrahydrofuran. The mixture is shaken vigorously and allowed to sit, stoppered, at room temperature overnight.

After filtering off the N,N'-dicyclohexylurea, 2 ml. of glacial acetic acid is added to the filtrate and the mixture allowed to stand 1 hour. After filtering, 200 ml. ether is added to the filtrate and the ether solution washed with 2 × 100 ml. saturated sodium bicarbonate solution and 3 × 100 ml. water and then dried over anhydrous soidum sulfate. The mixture is filtered, concentrated in vacuo to 25 ml. and chromatographed on a 150 g. acid washed alumina column using ether-petroleum ether 9v./v. 10–60%) as eluent to give phenyl 5-cyano-2-methyl-1-(p-methylsulfinylbenzylidenyl)-3-indenylacetate.

Similarly, using 2-(2-methoxyethoxy)-ethanol, glycol or N-acetyl-ethanolamine in place of phenol in the above procedure gives 2-(2-methoxyethoxy)-ethyl 5-cyano-2-methyl-1-(p-methylsulfinylbenzylidenyl)-3-indenylacetate, β-hydroxyethyl 5-cyano-2-methyl-1-(p-methylsulfinylbenzylidenyl)-3-indenylacetate and β-acetamidoethyl 5-cyano-2-methyl-1-(p-methylsulfinylbenzylidenyl)-3-indenylacetate, respectively.

A mixture of .06 mole of sodium 5-cyano-2-methyl-1-(p-methylsulfinylbenzylidene)-3-indenylacetate and 0.05 mole of trityl bromide in 100 ml. anhydrous benzene is refluxed with rapid stirring under nitrogen for 5 hours. The hot reaction mixture is filtered and the filtrate is concentrated in vacuo. The residue is recrystallized from methyl ethyl ketone to give trityl 5-cyano-2-methyl-1-(p-methylsulfinylbenzylidene)-3-indenylacetate.

EXAMPLE 7

N-[5-cyano-2-methyl-1-(p-methylsulfinylbenzylidene)-3-indenylacetyl]-glycine A. Benzyl-N-[5-cyano-2-methyl-1-(p-methylsulfinylbenzylidene)-3-indenylacetyl]-glycinate - The procedure of Example 6 is followed using benzylamino acetate to produce the above-named compound.

B. N-[5-cyano-2-methyl-1-(p-methylsulfinylbenzylidene)-3-indenylacetyl]-glycine - Benzyl-N-[5-cyano-2-methyl-1-(p-methylsulfinylbenzylidene)-3-indenylacetyl]-glycinate (0.003 mole) in a mixture of 25 ml. of anhydrous ethanol and 2.5 ml. of 1 N sodium hydroxide is allowed to stand at room temperature for 18 hours. The solution is diluted with water and extracted with ether. The aqueous layer is acidified with dilute hydrochloric acid and the organic product is extracted with ethyl acetate, washed with water and dried over sodium sulfate. Evaporation of the solution gives N-[5-cyano-2-methyl-1-(p-methylsulfinylbenzylidene)-3-indenylacetyl]-glycine.

EXAMPLE 8

A. Sodium 5-cyano-2-methyl-1-(p-methylsulfinylbenzylidene)-3-indenylacetate

5-Cyano-2-methyl-1-(p-methylsulfinylbenzylidene)-3-indenylacetic acid (1.6 g.) in methanol (10 ml.) is added to a solution of sodium methoxide (0.27 g.) in methanol (5 ml.). The reaction mixture is stirred for 20 minutes and evaporated to dryness to yield sodium 5-cyano-2-methyl-1-(p-methylsulfinylbenzylidene)-3-indenylacetate.

B. Calcium 5-cyano-2-methyl-1-(p-methylsulfinylbenzylidene)-3-indenylacetate The above reaction is repeated using 2 moles of acid per mole of calcium methoxide. Using the same reaction conditions and techniques there is obtained calcium 5-cyano-2-methyl-1-(p-methylsulfinylbenzylidene)-3-indenylacetate.

EXAMPLE 9

A mixture of 250 parts of 5-cyano-2-methyl-1-(p-methylsulfinylbenzylidene)-3-indenylacetic acid and 25 parts of lactose is granulated with suitable water and to this is added 100 parts of maize starch. The mass is passed through a 16-mesh screen. The granules are dried at a temperature below 60°C. The dry granules are passed through a 16-mesh screen and mixed with 3.8 parts of magnesium stearate. They are then compressed into tablets suitable for oral administration according to the method of this invention.

EXAMPLE 10

7-Cyano-2-methyl-1-(p-methylsulfinylbenzylidene)indenyl-3-acetic acid

A. Mixture of 2-methylnitroindanones

Potassium nitrate (35.25 g.) dissolved in cold concentrated sulfuric acid (290 ml.) is added over 3 hrs. to 2-methyl indanone (47.0 gm.) in cold concentrated sulfuric acid (80 ml.) so that the temperature never goes above 10°. After the end of these additions, the temperature is allowed to run up to room temperature and the reaction is stood for 4 hrs. longer and poured into ice-water. The aqueous solution is extracted with methylene chloride (3 × 400 ml.), the organic layers combined and washed with water (2 × 100 ml.), saturated sodium bicarbonate solution (2 × 200 ml.) and water again (1 × 200 ml.).

The organic layer is dried (MgSO$_4$), filtered and evaporated to dryness.

B. Mixtures of amino-2-methylindanones

The above mixture (31.5 g.) is hydrogenated in ethanol (200 ml.) over platinium oxide (0.2 gm.) at 40 p.s.i. and room temperature until the theoretical uptake of 2 moles of hydrogen indicates the reduction of the nitro group is complete. The solution is filtered and evaporated to ½ volume when the 6-amino-2-methyl indanone crystallizes out (8 gm.) m.p. 138°–140°. On evaporating the ethanol solution further a red oil remains which is mainly the 4-amino-2-methylindanone isomer.

C. 4-Cyano-2-methyl indanone

The 4-amino isomer obtained above (10.0 g., 0.002 ml). is dissolved in water (25 ml.) and concentrated hydrochloric acid (15 ml.) at 60° then cooled to 0°–5°. A solution of sodium nitrite (4.5 gm.) in ice water (50 ml.) is added in small portions. Sodium carbonate is added until pH 7 is reached and the solution added to an ice cold solution (0°) of cuprous cyanide (10.0 g.) sodium cyanide (15 gm.) in water (50 ml.) and toluene (50 ml.). The solution is brought to room temperature and then warmed to 50° for 1 hr. and left overnight at room temperature. The organic layer is separated, washed with water, an acidic solution of ferric chloride, and then water again. The organic layer is dried over anhydrous magnesium sulfate and filtered. The solvent is evaporated off to give crude 4-cyano-2-methyl indanone (84 gm.) as a red oil. Chromatography on silica gel (Baker Analyced 60–200 mesh) using ether petroleum ether mixtures as eluants gives pure 4-cyano-2-methyl indanone m.p. 101°–102°.

D. 7-Cyano-2-methyl-1-(p-methylsulfinylbenzylidene)-indenyl-3-acetic acid

Example 1, (C through E) is repeated on the above material as starting material to give the title compound m.p. 135°–140°.

EXAMPLE 11

5-Acetamido-2-methyl-1-(p-methylsulfinylbenzylidene)-indenyl-3-acetic acid

A. 6-Acetamido-2-methylindanone

6-Amino-2-methylindanone (0.1 mole), (Example 10 B above) acetic anhydride (0.11 mole) and pyridine (50 ml.) are stirred under nitrogen at room temperature overnight and then water (1 ml.) added. Stirring is continued for 30 minutes and the solution is evaporated to ⅓ volume under high vacuum at 40°, poured into ice water (40 ml.) and extracted with methylene chloride (2 × 200 ml.). The organic layers are combined and washed with 2.5 N hydrochloric acid (4 × 50 ml.), water (50 ml.) and dried (anhydrous MgSO$_4$). The solution is filtered and the filtrate evaporated to dryness to give 6-acetamide-2-methylindanone.

B. 5-Acetamido-2-methyl-1-(p-methylsulfinylbenzylidene)-indenyl-3-acetic acid Example 1 (C through E) is repeated on the product from the above reaction to obtain the title compound.

EXAMPLE 12

7-Acetamido-2-methyl-1-(p-methylsulfinylbenzylidene)-indenyl-3-acetic acid

A. 4-Acetamido-2-methylindanone

Example 11 A is repeated using 4-amino-2-methyl indanone in place of 6-amino-2-methylindanone to obtain the title compound.

B. 7-Acetamido-2-methyl-1-(p-methylsulfinylbenzylidene)-indenyl-3-acetic acid

Example 1 (C through E) is repeated on the above 4-acetamido-2-methyl indanone to obtain the title compound.

EXAMPLE 13

5-Acetoxy-2-methyl-1-(p-methylsulfinylbenzylidene)-indenyl-3-acetic acid

A. 6-Acetoxy-2-methylindanone

6-Amino-2-methylindanone (5.0 gm.), cocentrated hydrochloric acid (7.5 ml.) and water (15 ml.) are warmed to solution and then cooled to 0°–5°. To this is added sodium nitrate 92.25 gm.) in ice water (50 ml.). The diazonium salt solution is added at 0° to sodium borofluoride (20 gm.) in water (20 ml.). The precipitated solid is filtered, washed with water, methanol then ether. The solid is dried (5.9 gm.)

The salt in glacial acetic acid (50 ml.) is heated to reflux for 30 minutes and evaporated to dryness under reduced pressure to give crystaline 6-acetoxy-2-methylindanone (4.0 gm.). The product is hydrolyzed in 2.5 N sodium hydroxide (50 ml.) and methanol (10 ml.) under reflux for 10 minutes. The basic solution is extracted with ethyl acetate (4 × 100 ml.) acidified (dilute hydrochloric acid) and the aqueous layer extracted with ether to give the desired phenol (1.7 gm.) as a red oil.

B. 6-Methanesulfonyloxy-2-methylindanone

A mixture of the indanone above (5.0 gm.), methanesulfonyl chloride (3.7 gm.) and potassium carbonate (5.0 gm.) in acetone (50 ml.) is refluxed for 24 hrs. Ether (100 ml.) is added and the ether layer washed with water (2 × 50 ml.), dried (MgSO₄), filtered and evaporated to dryness to give the 6-methanesulfonyloxy-2-methylindanone (5.0 gm.) as a yellow oil.

C. Methyl 5-methylsulphonyloxy-2-methyl-indenyl-3-acetate

Example 1 C is repeated using an equivalent amount of 6-methanesulfonyloxy-2-methylindanone in place of 6-cyano-2-methyl indanone to give the title compound.

D. 5-Hydroxy-2-methyl-1-(p-methylsulfinylbenzylidene)-indenyl-3-acetic acid

Example 1 D is repeated using the compound from Example 13 C above in place of methyl 5-cyano-2-methyl-3-indenyl acetate during which the methanesulfonyl group is hydrolyzed off. Then Example 1 E is repeated on this product to obtain the title compound m.p. 192°–193° from ethyl acetate.

E. 5-Acetoxy-2-methyl-1-(p-methylsulfinylbenzylidene)-indenyl-3-acetic acid

The phenol above (Example 13 D), (0.1 mole) and acetic anhydride (0.22 mole) in pyridine (50 ml.) is reacted exactly as described for Example 11 A to give the 5-acetoxy-2-methyl-1-(p-methylsulfinylbenzylidene)-indenyl-3-acetic acid.

What is claimed is:

1. A compound of the formula

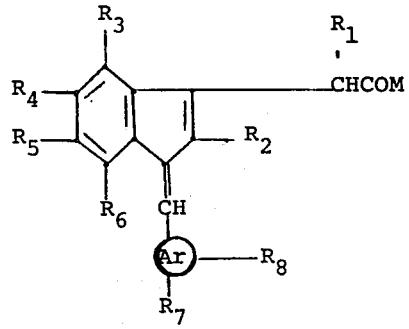

wherein:
Ar is phenyl;
$R_1$ is hydrogen, $C_{1-5}$ loweralkyl or halogenated $C_{1-5}$ loweralkyl;
$R_2$ is hydrogen or $C_{1-5}$ loweralkyl;
$R_3$, $R_4$, $R_5$ and $R_6$ are each hydrogen, $C_{1-5}$ loweralkyl, $C_{1-5}$ loweralkanoyloxy, benzyloxy, $C_{1-5}$ loweralkoxy, nitro, amino, $C_{1-5}$ loweralkanoylamino, benzoylamino, $C_{1-5}$ loweralkylamino, di-$C_{1-5}$ loweralkylamino, di-$C_{1-5}$ loweralkylaminoalkyl, sulfamyl, $C_{1-5}$ loweralkylthio, mercapto, halogen, hydroxy, hydroxy $C_{1-5}$ loweralkyl, $C_{1-5}$ loweralkylsulfonyl, carboxyl, carb $C_{1-5}$ loweralkoxy, carbamido, halogeno $C_{1-5}$ loweralkyl, at least one of $R_3$-$R_6$ being $C_{1-5}$ loweralkanoyloxy, benzoyloxy, $C_{1-5}$ loweralkanoylamino or benzoylamino;
$R_7$ may be $C_{1-5}$ loweralkyl or $C_{1-5}$ loweralkylsulfonyl;
$R_8$ may be hydrogen, halogen, hydroxy, $C_{1-5}$ loweralkoxy or halo $C_{1-5}$ loweralkyl; and
M may be hydroxy, $C_{1-5}$ loweralkoxy and the pharmaceutically acceptable acid salts.

2. The compound of claim 1 wherein
$R_1$ is hydrogen;
$R_2$ is methyl;
$R_3$, $R_5$ and $R_6$ are each hydrogen;
$R_4$ is acetoxy;
$R_7$ is p-methylsulfinyl;
$R_8$ is hydrogen; and
M is hydroxy.

3. The compound of claim 1 wherein
$R_1$ is hydrogen or $C_{1-5}$ loweralkyl;
$R_2$ is $C_{1-5}$ loweralkyl;
$R_3$, $R_4$, $R_5$ and $R_6$ are each hydrogen, $C_{1-5}$ loweralkanoyloxy, benzoyloxy, $C_{1-5}$ loweralkanoylamino, benzoylamino, fluoro, $C_{1-5}$ loweralkoxy or di-$C_{1-5}$ loweralkylamino, no more than two of $R_3$, $R_4$, $R_5$ and $R_6$ being other than hydrogen;
$R_7$ is methylsulfinyl or methylsulfonyl;

$R_8$ is hydrogen; and
M is hydroxy or $C_{1-5}$ loweralkoxy.

4. The compound of claim 3 wherein
$R_1$ is hydrogen;
$R_2$ is $C_{1-5}$ loweralkyl;
$R_7$ is methylsulfinyl; and
M is hydroxy.

5. The compound of claim 4 wherein
$R_3$ and $R_6$ are each hydrogen;
$R_4$ and $R_5$ are each hydrogen, $C_{1-5}$ loweralkanoyloxy, fluoro, $C_{1-5}$ loweralkoxy, di-$C_{1-5}$ loweralkylamino, $C_{1-5}$ loweralkanoylamino or benzoylamino.

* * * * *